United States Patent [19]

Turk

[11] Patent Number: 5,507,770
[45] Date of Patent: Apr. 16, 1996

[54] INTRALUMINAL GRAFTING STENT AND METHOD FOR IMPLANTING SAME IN A BLOOD VESSEL

[75] Inventor: Rodney E. Turk, West Bloomfield, Mich.

[73] Assignee: Aeroquip Corporation, Maumee, Ohio

[21] Appl. No.: 344,120

[22] Filed: Nov. 23, 1994

[51] Int. Cl.⁶ ............................................. A61B 19/00
[52] U.S. Cl. ................................. 606/198; 606/191
[58] Field of Search ........................... 623/1, 11, 12; 606/1, 190–198

[56] References Cited

U.S. PATENT DOCUMENTS

| | | |
|---|---|---|
| 4,195,623 | 4/1980 | Zeff et al. . |
| 4,195,637 | 4/1980 | Gruntzig et al. . |
| 4,271,839 | 6/1981 | Fogarty et al. . |
| 4,386,601 | 6/1983 | Trick . |
| 4,508,112 | 4/1985 | Seeler . |
| 4,577,631 | 3/1986 | Kreamer . |
| 4,649,914 | 3/1987 | Kowalewski . |
| 4,733,665 | 3/1988 | Palmaz . |
| 4,739,762 | 4/1988 | Palmaz . |
| 4,740,207 | 4/1988 | Kreamer ........................ 623/1 |
| 4,762,130 | 8/1988 | Fogarty et al. . |
| 4,769,029 | 9/1988 | Patel ............................ 623/1 |
| 4,774,949 | 10/1988 | Fogarty . |
| 4,776,337 | 10/1988 | Palmaz . |
| 4,787,899 | 11/1988 | Lazarus ........................ 623/1 |
| 4,793,348 | 12/1988 | Palmaz . |
| 4,795,458 | 1/1989 | Regan ........................... 623/1 |
| 4,877,025 | 10/1989 | Hanson . |
| 4,955,895 | 9/1990 | Sugiyama et al. ............ 606/194 |
| 5,156,620 | 10/1992 | Pigott ........................... 623/1 |

*Primary Examiner*—Stephen C. Pellegrino
*Assistant Examiner*—Glenn Dawson
*Attorney, Agent, or Firm*—Emch, Schaffer, Schaub & Porcello Co.

[57] ABSTRACT

An intraluminal grafting stent that includes a collapsible tube member having a first end and a second end. An outer wall and an inner wall extend between the ends. A first end wall and a second end wall extend between the outer wall and the inner wall. The outer, inner, first end and second end wall form a chamber. A permeable film layer extends between the first end wall and the second end wall in the chamber. The film layer, outer wall and end walls define a space. A composite material is positioned in a chamber between the inner wall and the permeable film layer. An opening is positioned in one of the end walls to allow the introduction of a reagent into the defined space. The reagent reacts with the composite material to cause the composite material to harden after the intraluminal grafting stent has been positioned in a blood vessel. The present invention is further directed to a method for implanting the intraluminal grafting stent in a blood vessel. Using a balloon catheter.

10 Claims, 3 Drawing Sheets

5,507,770

INTRALUMINAL GRAFTING STENT AND METHOD FOR IMPLANTING SAME IN A BLOOD VESSEL

BACKGROUND OF THE INVENTION

The present invention is directed to an intraluminal grafting stent. More specifically, the present invention is directed to an intraluminal grafting stent that can be implanted in a blood vessel at the site of aortic aneurysms. It can also provide support for diseased blood vessels.

Intraluminal support devices are known in the art. For example, an intraluminal graft/stent is disclosed in U.S. Pat. No. 5,156,620, which is incorporated herein by reference.

SUMMARY OF THE INVENTION

The present invention is directed to an intraluminal grafting stent. The grafting stent includes a collapsible tube member having a first end and a second end. An outer wall and an inner wall extend between the ends. A first end wall and a second end wall extend between the outer wall and the inner wall. The outer, inner, first end and second end walls form a chamber.

A permeable film layer extends between the first end wall and the second end wall in the chamber. The film layer, outer wall and end walls define a space.

A composite material is positioned in the chamber between the inner wall and the permeable film layer. An opening is positioned in one of the end walls to allow the introduction of a reagent into the defined space. The reagent reacts with the composite material to cause the composite material to harden after the intraluminal grafting stent has been positioned in a blood vessel.

The present invention is further directed to a method for implanting an intraluminal grafting stent in a blood vessel. The steps are as follows:

(a) placing an expandable catheter in an intraluminal grafting stent comprised of a collapsible tube member having a first end and a second end, an outer wall and an inner wall extending between the ends, a first end wall and a second end wall extending between the outer wall and an inner wall, the outer, inner, first end and second end walls forming a chamber, one of the end walls defining an opening, the chamber containing a composite material, the catheter being adjacent to the inner wall;

(b) inserting the intraluminal grafting stent in a blood vessel by the catheter;

(c) expanding the catheter to cause the collapsible tube member to expand at a site in the blood vessel where the grafting stent is to be implanted;

(d) introducing a reagent in the opening;

(e) permitting the reagent to react with the composite material to cause the composite material to harden;

(f) collapsing the catheter; and (g) removing the catheter from the blood vessel.

The primary object of the present invention is to provide a superior intraluminal grafting stent and method of implantation that is effective in the repair of blood vessels.

An important object of the present invention is to provide an intraluminal grafting stent that is relatively easy to use.

Other objects and advantages of the present invention will become apparent upon a review of the drawings and the following detailed description of the invention.

DETAILED DESCRIPTION OF THE INVENTION

Figure 1:
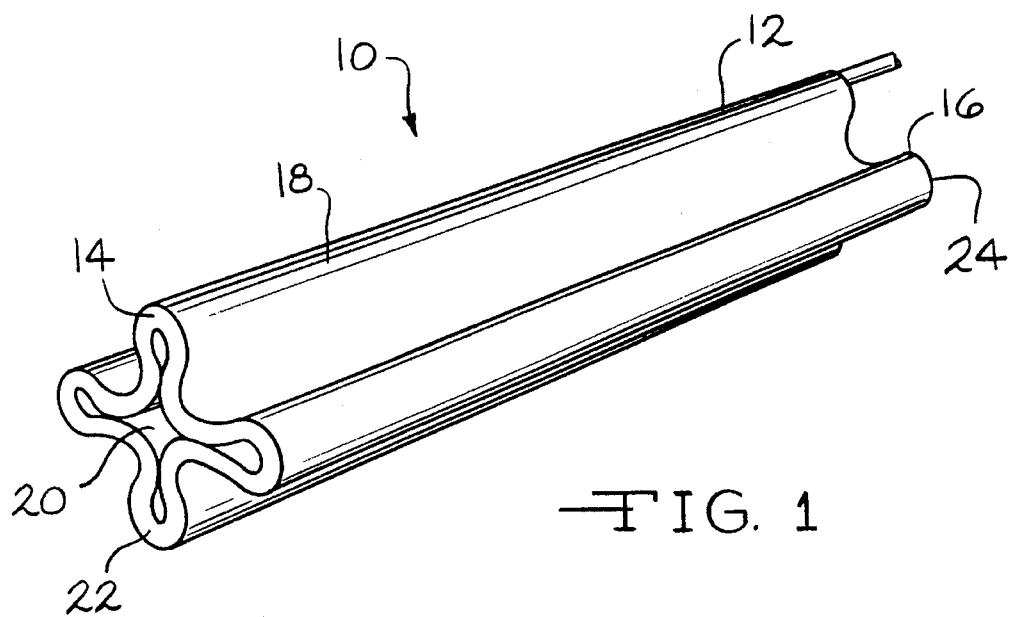
FIG. 1 is a perspective view of the intraluminal grafting stent according to the present invention in a collapsed condition.
Figure 2:
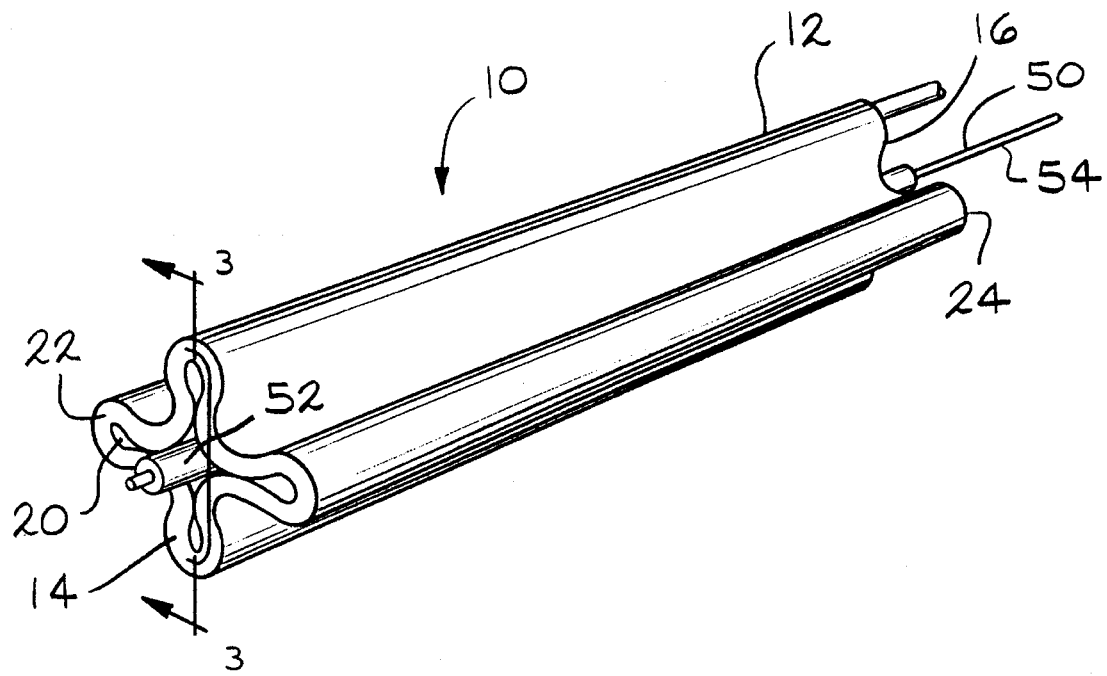
FIG. 2 is a perspective view similar to the view of FIG. 1 with a collapsible catheter positioned in the grafting stent.
Figure 3:
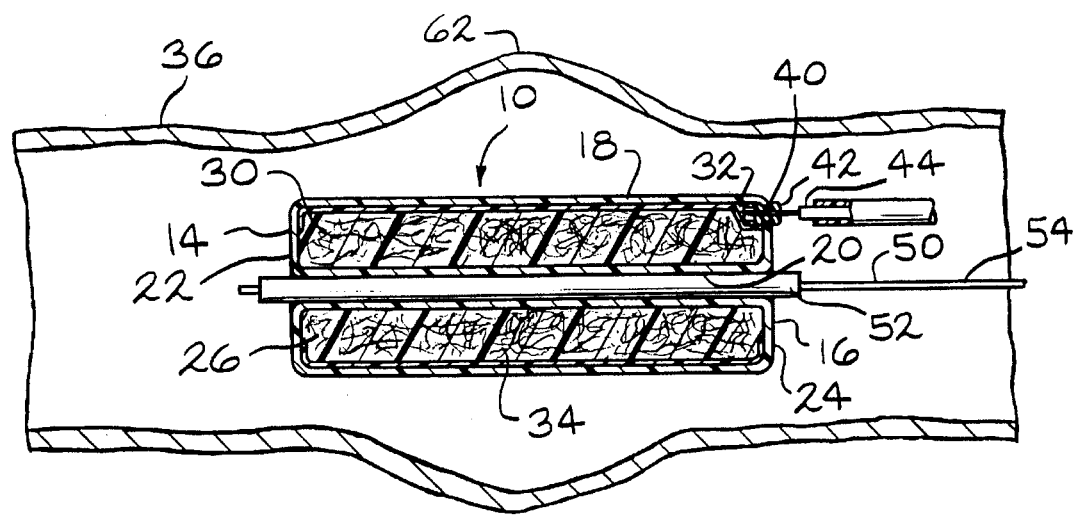
FIG. 3 is a cross-sectional view taken along line 3—3 of FIG. 2 showing the grafting stent positioned at the implantation site of the blood vessel with an injection device for the reagent positioned in the opening of the side wall.

Referring now to the drawings, the intraluminal grafting stent is indicated by the reference number 10. As shown in FIG. 1–3, the intraluminal grafting stent 10 includes a collapsible tube member 12. The tube member 12 includes a first end 14 and a second end 16. An outer wall 18 and an inner wall 20 extend between the ends 14 and 16. The inner wall 20 defines a hollow space. A first end wall 22 and a second end wall 24 extend between the outer wall 18 and the inner wall 20. As shown in FIG. 3, the outer, inner, first end and second end walls 18, 20, 22 and 24, respectively, form a chamber 26. The walls 18, 20, 22 and 24 of the tube member 12 are formed of a flexible, semi-rigid polymer material such as polytetrafluoroethylene or some other suitable biocompatible material.

As shown in FIGS. 1 and 2, the tube member 12 in its collapsed condition can be formed in a "clover-leaf" cross-sectional shape. It has been found that this shape allows the intraluminal grafting stent 10 to be manipulated easily in a blood vessel. It should be understood, however, that the tube member 12 can be formed in a variety of shapes.

As shown in FIG. 3, a permeable film layer 30 extends between the first end wall 22 and the second end wall 24 in the chamber 26. The film layer 30, the outer wall 18, the first end wall 22 and the second end wall 24 define a variable space 32 in the chamber 30. The permeable film layer 30 can be made of a skived, blown or drawn layer of polyethylene, polyurethane, synthetic resin polymers and products, or other suitable polymer material having apertures or micropores. An example of a material that can be used in the construction of the film layer 30 is a microporus polymer material coated with a material such as expanded polyetrafluoroethylene (ePTFE) sold under the trademark GORETEX®. The permeable film layer 30 allows for the even dispersion of the reagent as described below.

As shown in FIG. 3, a composite material 34 is positioned in the chamber 26 between the inner wall 20 and the permeable film layer 30. The composite material can consist of a suitable material that can be hardened, as described below, to implant the grafting stent 10 in a blood vessel 36. An example of a suitable composite material is an epoxy resin, such as one sold under the designation "568 B" by Aremco Products of Ossining, N.Y. Another example of a suitable composite material is a thermosetting polymer material. Examples of suitable polymer materials are a polyurethane material sold under the trademark PLURA- COL P® and a silicon material sold under the trademark SILASTIC®. The composite material 34 can be used with or without fiber reinforcement. If fibers are used, they can be drawn-fiber glass or other high modulus fiber woven into a fabric sheath.

Still referring to FIG. 3, the intraluminal grafting stent 10 includes an opening 40 between the defined space 32 and the exterior of the grafting stent. As shown in the embodiment of FIG. 3, the opening 40 includes a one-way valve 42, such as a check valve, to receive an injection device 44. The one-way valve 42 allows materials to enter through the opening 40 into the chamber 26 but prevents the materials from escaping through the opening 40.

As shown in FIGS. 3–6, and as described in detail below concerning the method of the present invention, an expandable catheter 50 is positioned within the collapsible tube member 12. The catheter 50 is expanded to cause the tube member 12 to expand at the site of implantation in the blood vessel. A reagent 60 is introduced through opening 40 into the defined space 32. The reagent can be a polymerizing agent that can react with the particular composite material 34 to cause the material to harden. The type of reagent used depends on the type of composite material 34 used in the grafting stent 10. For example, a reagent sold under the designation "568 A" reacts with the above-described epoxy resin. The polyurethane polymer material reacts with a weak acid salt catalyst. The silicon polymer material reacts with a platinum hydrosiliation catalyst. It will be readily apparent to one skilled in the art that many types of composite materials and reagents can be used in the present invention depending on the application. The reagent 60 permeates the permeable film layer 30 and reacts with the composite material 34. The composite material 34 is permitted to harden for a predetermined period of time. The catheter 50 is then collapsed and removed from the tube member 12 and the blood vessel 36. The injection device 44 is also removed. The intraluminal grafting stent 10 provides repair and support for the blood vessel at the site of implantation.

Referring still to FIGS. 3–6, the method of the present invention will be described in detail. As shown in FIG. 3, an expandable catheter 50 is placed in the intraluminal grafting stent 10 adjacent to the inner wall 20. The catheter 50 includes a balloon portion 52 and a hollow guide wire 54. When the grafting stent 10 is positioned on the catheter 50, it can be guided through the blood vessel 36 by the guide wire 54.

Figure 4:
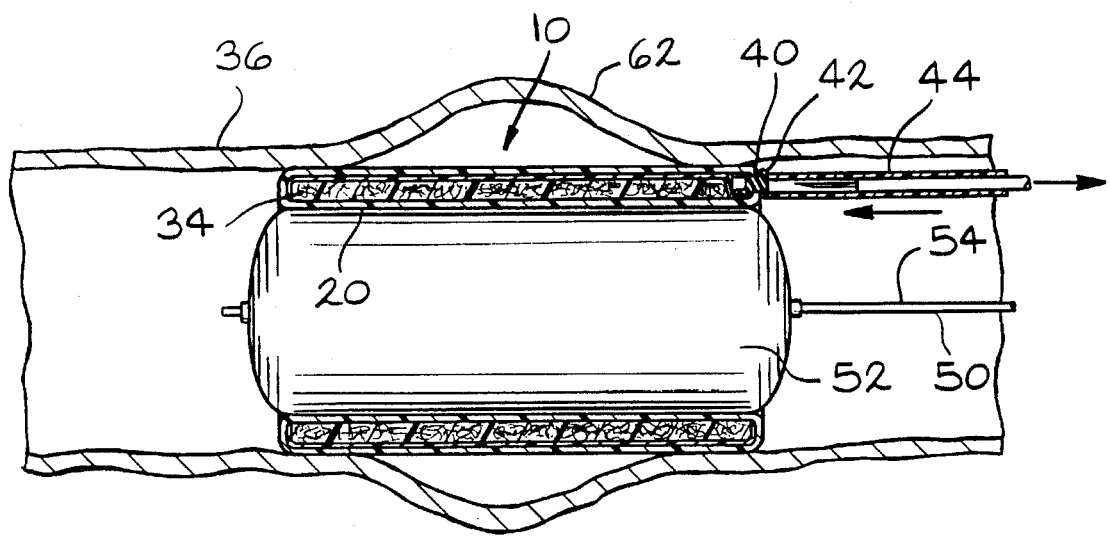
FIG. 4 is a cross-sectional view similar to the view of FIG. 3 showing the grafting stent being expanded by the catheter.

As shown in FIG. 4, the balloon portion 52 of the catheter 50 is expanded to cause the collapsible tube member 12 of the graft 10 to expand at a predetermined site 62 on the blood vessel 36 where the graft is to be implanted.

Figure 5:
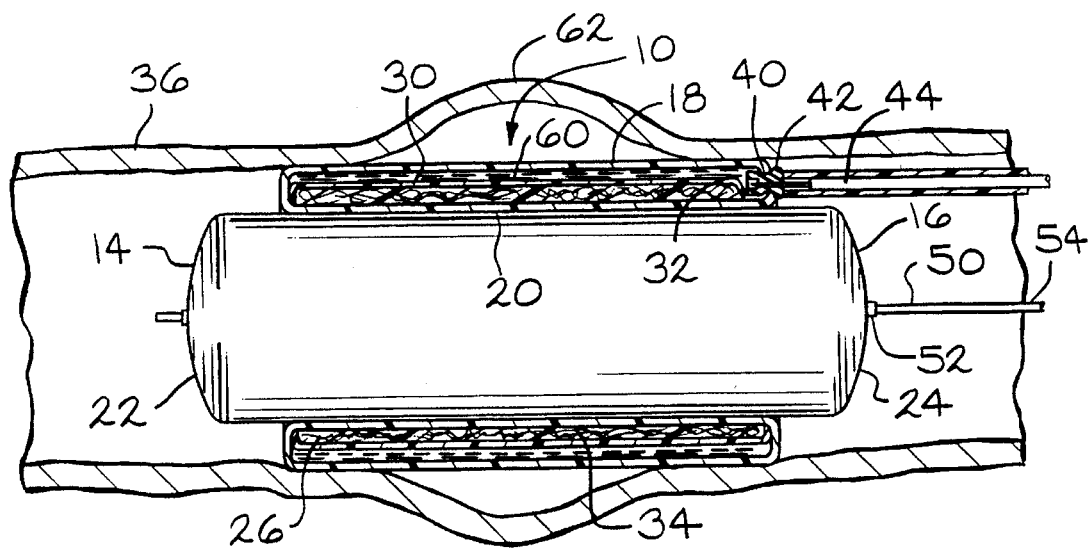
FIG. 5 is a cross-sectional view similar to the view of FIG. 4 showing the reagent being injected into the chamber.

As shown in FIG. 5, a reagent 60, as described above, is introduced into the defined space 32 through the valve 42 in opening 40 by an injection device 44. The reagent 60 permeates the permeable film layer 30 and begins to react with the composite material 34, as described above.

There is a waiting period for a predetermined period of time to permit the reagent 60 to react with the composite material to harden. The balloon portion 52 of the catheter 50 is then allowed to collapse. The catheter 50 is then removed from the blood vessel 36. The injection device 44 is also removed from the blood vessel 36. The one-way valve 42 prevents the escape of materials from the opening 40.

Figure 6:
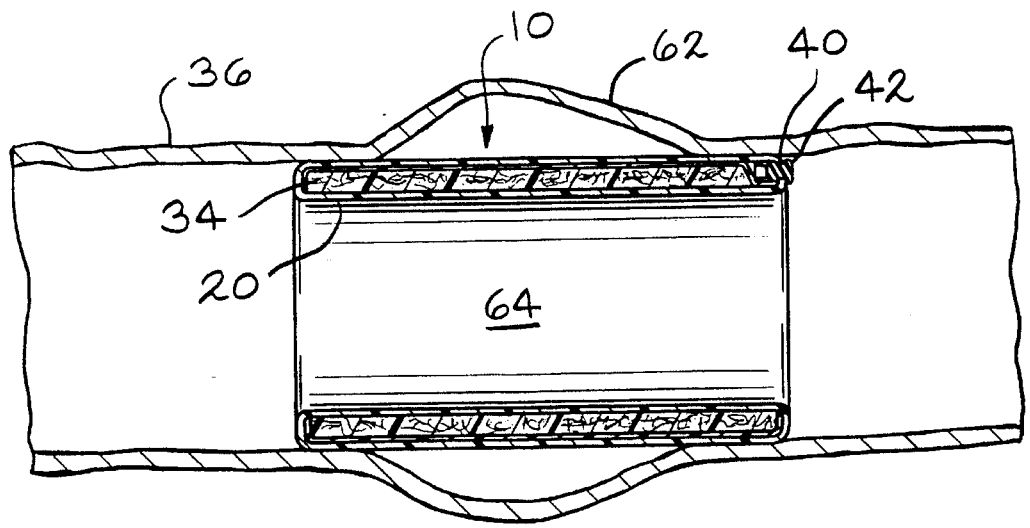
FIG. 6 is a cross-sectional view similar to the view of FIG. 5 showing the grafting stent implanted in the blood vessel.

As shown in FIG. 6, the grafting stent 10 when implanted provides repair and support for the blood vessel 36 at the site 62 of repair. Blood can flow through the pathway 64 formed by the inner wall 20 of the grafting stent.

It should be understood that many changes can be made to the present invention as described herein without departing from the scope of the appended claims.

I claim:

1. An intraluminal grafting stent for use in a blood vessel comprising, in combination:

a collapsible tube member having a first end and a second end, an outer wall and an inner wall extending between said ends, a first end wall and a second end wall extending between said outer wall and an inner wall, said outer, inner, first end and second end walls forming a chamber;

a permeable film layer extending between said first end wall and said second end wall in said chamber, said film layer, said outer wall and said end walls defining a space;

a composite material positioned in said chamber between said inner wall and said permeable film layer;

an opening in one of said end walls for introducing a reagent into said defined space;

whereby when said grafting stent is inserted in a blood vessel, said collapsible tube member is expanded by an expandable catheter, a reagent is introduced through said opening, said reagent travels through said permeable film layer, said composite material reacts with said reagent causing said material to harden to allow said graft to support said blood vessel.

2. The intraluminal grafting stent of claim 1, wherein said collapsible tube member is comprised of a polymer material.

3. The intraluminal grafting stent of claim 1, wherein said permeable film layer is comprised of a polymer material having apertures.

4. The intraluminal grafting stent of claim 1, wherein said composite material is comprised of an epoxy resin.

5. The intraluminal grafting stent of claim 1, wherein said composite material is a thermosetting polymer material.

6. The intraluminal grafting stent of claim 1, wherein said reagent is a polymerizing agent that reacts with said composite material to harden said composite material.

7. A method for implanting an intraluminal grafting stent in a blood vessel comprising the steps of:

(a) placing an expandable catheter in an intraluminal grafting stent comprised of a collapsible tube member having a first end and a second end, an outer wall and an inner wall extending between said ends, a first end wall and a second end wall extending between said outer wall and said inner wall, said outer, inner, first end and second end walls forming a chamber, one of said end walls defining an opening, said chamber containing a composite material, said catheter being adjacent to said inner wall;

(b) inserting said intraluminal grafting stent in a blood vessel by said catheter;

(c) expanding said catheter to cause said collapsible tube member to expand at a site in said blood vessel where said grafting stent is to be implanted;

(d) introducing a reagent in said opening;

(e) permitting said reagent to react with said composite material to cause said composite material to harden;

(f) collapsing said catheter; and (g) removing said catheter from said blood vessel.

8. The method for implanting an intraluminal grafting stent of claim 7, wherein said composite material is comprised of an epoxy resin.

9. The method for implanting an intraluminal grafting stent of claim 7, wherein said composite material is comprised of a thermosetting polymer material.

10. The method for implanting an intraluminal grafting stent of claim 7, wherein said reagent is a polymerizing agent that reacts with said composite material to harden said composite material.

* * * * *